US009968542B2

(12) United States Patent
Kishina et al.

(10) Patent No.: US 9,968,542 B2
(45) Date of Patent: May 15, 2018

(54) MAKEUP BASE FOR SKIN REMOVABLE WITH WARM WATER

(71) Applicant: SHISEIDO COMPANY, LTD., Tokyo (JP)

(72) Inventors: Takahiro Kishina, Kanagawa (JP); Katsuyuki Kaneko, Kanagawa (JP); Amane Tatsuta, Kanagawa (JP); Yukiko Sato, Kanagawa (JP); Minako Shudo, Kanagawa (JP); Masahiko Yamaguchi, Kanagawa (JP); Hiroyo Usuki, Kanagawa (JP); Mikino Nosaka, Kanagawa (JP); Nozomi Takeshita, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days. days.

(21) Appl. No.: 14/434,249

(22) PCT Filed: Oct. 11, 2013

(86) PCT No.: PCT/JP2013/077739
§ 371 (c)(1),
(2) Date: Apr. 8, 2015

(87) PCT Pub. No.: WO2014/058048
PCT Pub. Date: Apr. 17, 2014

(65) Prior Publication Data
US 2015/0272853 A1    Oct. 1, 2015

(30) Foreign Application Priority Data

Oct. 12, 2012 (JP) ................................. 2012-227165

(51) Int. Cl.
| | | |
|---|---|---|
| A61K 8/81 | (2006.01) | |
| A61K 8/60 | (2006.01) | |
| A61K 8/86 | (2006.01) | |
| A61K 8/34 | (2006.01) | |
| A61Q 1/02 | (2006.01) | |
| A61Q 1/14 | (2006.01) | |
| A61K 8/06 | (2006.01) | |

(52) U.S. Cl.
CPC ............ *A61K 8/8135* (2013.01); *A61K 8/062* (2013.01); *A61K 8/345* (2013.01); *A61K 8/60* (2013.01); *A61K 8/86* (2013.01); *A61Q 1/02* (2013.01); *A61Q 1/14* (2013.01); *A61K 2800/59* (2013.01)

(58) Field of Classification Search
None
See application file for complete search history.

(56) References Cited

U.S. PATENT DOCUMENTS

| 5,238,678 A | 8/1993 | Shiozawa | |
|---|---|---|---|
| 6,010,686 A * | 1/2000 | De La Poterie | ....... A61K 8/044 424/401 |
| 6,946,518 B2 * | 9/2005 | De La Poterie | ..... A61K 8/8152 524/504 |
| 2002/0085986 A1 | 7/2002 | Collin | |
| 2003/0003154 A1 | 1/2003 | De La Poterie | |
| 2003/0086887 A1 | 5/2003 | Auguste | |
| 2003/0118542 A1 | 6/2003 | De La Poterie | |
| 2003/0207817 A1 | 11/2003 | Ide | |
| 2005/0201958 A1 | 9/2005 | De La Poterie | |
| 2006/0078520 A1 * | 4/2006 | Pays | ...................... A61K 8/027 424/70.7 |
| 2007/0190014 A1 | 8/2007 | Ide | |
| 2008/0081029 A1 * | 4/2008 | Nishihama | ............... A61K 8/11 424/69 |

FOREIGN PATENT DOCUMENTS

| CN | 1762328 | | 4/2006 | |
|---|---|---|---|---|
| EP | 1103250 | A1 | 5/2001 | |
| EP | 1201222 | A1 | 5/2002 | |
| EP | 1269987 | A1 | 1/2003 | |
| GB | 1110240 | A * | 4/1968 | ............... A61K 8/25 |
| JP | 525021 | | 2/1993 | |
| JP | 10236919 | A2 | 9/1998 | |
| JP | 11349441 | A2 | 12/1999 | |

(Continued)

OTHER PUBLICATIONS

Wikipedia entry for "Polysorbate" last updated Apr. 9, 2015; https://en.wikipedia.org/wiki/Polysorbate.*
Wikipedia entry for "Hydrophilic-lipophilic balance," last updated May 9, 2016; https://en.wikipedia.org/wiki/Hydrophilic-lipophilic_balance.*
Quora "What is the temperature of warm water?" accessed 2016; https://www.quora.com/What-is-the-Temperature-of-warm-water.*
International Search Report dated Jan. 14, 2014 filed in PCT/JP2013/077739.
Extended European Search Report dated Mar. 8, 2016 issued in the corresponding European patent application No. 13845869.0.
William C. Griffin, "Calculation of HLB values of non-ionic surfactants", Journal of the Society of Cosmetic Chemists, May 14, 1954, vol. 5, pp. 249-256.; Cited in Taiwanese Search Report.

*Primary Examiner* — David J Blanchard
*Assistant Examiner* — Alissa Prosser
(74) *Attorney, Agent, or Firm* — Hankin, Hill & Clark LLP (57) ABSTRACT

A makeup base for skin that is applied to the skin before applying a makeup cosmetic is provided. The makeup base is not smeared or removed by sweat or cold water, but, when rubbed with warm water, is easily removed from the skin together with the makeup cosmetic and without using a cosmetic cleanser. The makeup base includes a water-containing aqueous phase as a continuous phase, which includes (a) a vinyl acetate polymer, (b) polyhydric alcohol, and (c) a hydrophilic nonionic surfactant. The (a) the vinyl acetate polymer is 0.5 to 7 mass % in the makeup base and is dispersed as particles in the aqueous phase, (b) the polyhydric alcohol is 0.5 to 5.5 parts by mass relative to 1 part by mass of (a) the vinyl acetate polymer, and (c) the hydrophilic nonionic surfactant is 1 to 5 mass % in the makeup base.

3 Claims, 1 Drawing Sheet

(56) References Cited

FOREIGN PATENT DOCUMENTS

| | | |
|---|---|---|
| JP | 200326539 | 1/2003 |
| JP | 2003137732 A2 | 5/2003 |
| JP | 2003238355 A2 | 8/2003 |
| JP | 2004339082 A2 | 12/2004 |
| JP | 2006306849 A2 | 11/2006 |
| JP | 200837826 | 2/2008 |
| JP | 2008266249 A2 | 11/2008 |
| JP | 2011168583 A2 | 9/2011 |
| JP | 2011225534 A2 | 11/2011 |
| WO | WO 9843523 A1 * 10/1998 | ............... A47K 7/02 |
| WO | WO 2011071795 A1 * 6/2011 | ............. A61K 8/585 |

* cited by examiner

MAKEUP BASE FOR SKIN REMOVABLE WITH WARM WATER

FIELD OF THE INVENTION

The present invention relates to a makeup base for skin, particularly a makeup base for skin that is removable with warm water and capable of removing makeup together with the makeup base with warm water by applying to the skin before makeup such as a foundation.

BACKGROUND OF THE INVENTION

Makeup such as foundation and the like usually contain a large amount of oil and other oil components. Therefore, it is necessary to use a makeup remover, a face wash, and the like, to remove makeup. Further, so-called long lasting type or waterproof type foundations, which have significantly improved water resistance, sebum resistance, durability of makeup, and the like, have a formula that is hardly removable with a common makeup remover or a face wash, and thus may often require a specially prepared makeup remover.

Use of a makeup remover or a face wash for removing makeup is one of the burdens for users in terms of time and cost, and some users concern themselves about the irritation to eyes or skin caused by a makeup remover or a face wash.

Therefore, the burdens and concerns of users may be reduced if makeup can be removed without using a makeup remover or a face wash.

In recent years, cosmetics removable with water or hot water have been studied.

For example, Patent Literature 1 discloses an oil-in-water eye makeup cosmetic easily removable with water or warm water. The art of Patent Literature 1 is one which the makeup base can be removed easily with water or warm water by blending the liquid crystal of a polyhydric alcohol and an amphipathic substance to an oil phase.

However, since the cosmetic of Patent Literature 1 is removable with water, it may be removed or come off with sweat or tears. Further, Patent Literature 1 merely discloses an eye makeup cosmetic, which is a partial makeup cosmetic applied to eyelashes, eyebrows or a part of an eyelid, but not a cosmetic applied throughout the entire skin of a face.

In contrast, Patent Literatures 2 and 3 disclose a cosmetic having a resistance against cold water of 30° C. or lower but easily removable by simply rubbing with warm water of 35 to 50° C.

Namely, Patent Literature 2 discloses a makeup cosmetic containing at least one hydrophobic film-forming polymer and a specific ionic surfactant in a cosmetically acceptable medium. The art of Patent Literature 2 is one which the specific ionic surfactant has an electroconductivity fluctuation in water of 100 µS/cm or more at 20 to 45° C. and thus the polymer film becomes sensitive to water, resulting in that while a resistance against cold water is maintained, a makeup film becomes brittle, disintegrates easily and peels off from a substrate when rubbed while in contact with warm water.

Further, Patent Literature 3 discloses a makeup cosmetic containing, in physiologically acceptable medium, a first semi-crystalline polymer having a melting point of 30° C. or higher and a second film forming polymer capable of forming a hydrophobic film at room temperature. The art of Patent Literature 3 is one which the film becomes easily affected by water when it exceeds a melting point of the first semi-crystalline polymer as the first semi-crystalline polymer has a melting point at 30° C. or higher. As a result, the film becomes brittle when it gets in contact with warm water and quickly breaks to come off from a substrate when rubbed.

Although Patent Literatures 2 and 3 disclose that the art may be applied to foundation and the like, only mascara is disclosed a specific example.

On the other hand, a wide variety of products in makeup cosmetics already exist in accordance with required color tone, feeling in use, feeling in finish, functions, and the like.

Therefore, if a makeup base that is hard to remove by water of low temperature such as sweat and the like and can be easily removed with warm water becomes available, users may use their preferable products after applying the makeup base. They will not be forced to change their preferences and remove makeup only with warm water without using a makeup remover, a face wash and the like.

Patent Literature 4 discloses a mascara base easily removable with water containing a water soluble polyacrylic acid polymer, polyvinylpyrrolidone and water, and also discloses that the mascara base, together with a mascara applied thereonto, is removable by simply washing with water without using a makeup remover.

However, as in Patent Literature 1, the mascara base of Patent Literature 4 may be smeared or removed by sweat or tears since it is also a water removable type. Further, the mascara base of Patent Literature 4 is an eyelash cosmetic, and a makeup base for skin applied to a wide area of the skin before applying foundation and the like, is not disclosed.

PRIOR ART

Patent Literature

Patent literature 1: Japanese Unexamined Patent Publication No. 2006-306849
Patent literature 2: Japanese Unexamined Patent Publication No. 2003-137732
Patent literature 3: Japanese Unexamined Patent Publication No. 2003-26539
Patent literature 4: Japanese Unexamined Patent Publication No. 2004-339082

DISCLOSURE OF THE INVENTION

Problem to be Solved by the Invention

The present invention was made in view of the above-described conventional art. An object of this invention is to provide a makeup base that is applied to the skin before applying foundation and the like, and that is not smeared or removed by sweat or cold water, but easily removed from the skin together with the makeup without using a cleanser such as a makeup remover or a face wash when rubbed with warm water.

Means to Solve the Problem

The present inventors have diligently studied to achieve the above-described object. As a result, the present inventors found that when predetermined amounts of a vinyl acetate polymer, polyhydric alcohol, and a hydrophilic nonionic surfactant are used, the above-described makeup base for skin may be obtained.

More specifically, the makeup base for skin according to the present invention is a makeup base for skin applied to the skin before applying a makeup cosmetic for skin, the makeup base comprising a water-containing aqueous continuous phase and containing
 (a) a vinyl acetate polymer,
 (b) polyhydric alcohol, and
 (c) a hydrophilic nonionic surfactant,
wherein (a) the vinyl acetate polymer is 0.5 to 7 mass % in the makeup base and is dispersed as particles in the aqueous phase, (b) the polyhydric alcohol is 0.5 to 5.5 parts by mass relative to 1 part by mass of (a) the vinyl acetate polymer, and (c) the hydrophilic nonionic surfactant is 1 to 5 mass % in the makeup base.

The above-described makeup base for skin may be removed with warm water of 38 to 45° C. when removing the makeup cosmetic for skin from the skin.

The makeup base for skin of the present invention is applied to the skin before makeup such as foundation, but not a makeup base for eyelashes or eyebrows. Further, makeup cosmetics such as foundation usually contain a large amount of colorants, but the present invention hardly contains colorants as it is a makeup base. In the makeup base for skin of the present invention, the colorants (colored pigments, white pigments, extender pigments, pigments, and the like) are less than 3 mass %, preferably less than 1 mass %, in total. On the other hand, a makeup cosmetic for skin applied onto the makeup base for skin of the present invention may contain colorants (colored pigments, white pigments, extender pigments, pigments, and the like) in 1 mass % or more, further 3 mass % or more, in total. Examples of the makeup cosmetic for skin applied after the makeup base for skin of the present invention include liquid foundation, cream foundation, powdery foundation, cheek (cheek color), facial powder, eyeshadow, concealer, lipstick, lip gloss and the like.

Further, the present invention provides the above-described makeup base for skin, wherein (b) the polyhydric alcohol is one or more selected from the group consisting of dipropylene glycol, propylene glycol, 1,3-butylene glycol, and polyethylene glycol.

Furthermore, the present invention provides the above-described makeup base for skin, wherein (c) the hydrophilic nonionic surfactant is a nonionic surfactant having an HLB of 8 or higher.

Furthermore, the present invention provides the above-described makeup base for skin, wherein (c) the hydrophilic nonionic surfactant is a sucrose fatty acid ester.

Furthermore, the present invention provides the makeup base for skin described in any of the above, wherein the makeup base is an O/W emulsion that and oil phase particles are dispersed in the aqueous phase separately from vinyl acetate polymer particles.

Furthermore, the present invention provides the makeup base for skin described in any of the above, which does not contain an ionic surfactant.

Furthermore, a makeup method of the present invention comprises a step of applying the makeup base for skin described in any of the above to the skin before applying a makeup cosmetic for skin, and a step of removing the above-described makeup cosmetic together with the makeup base, by rubbing the skin with warm water of 38 to 45° C. to remove the above-described makeup cosmetic.

In the above-described makeup method, it is preferable that warm water does not contain cleansers.

Effect of the Invention

According to the present invention, a makeup base for skin is provided which is not removed or does not come off with sweat, tears and low temperature water but can easily be removed from the skin while disintegrating homogeneously and finely when simply rubbed with warm water without using a cleanser such as a makeup remover or a face wash. By applying the base makeup for skin of the present invention before a makeup cosmetic for skin such as foundation and the like, the makeup cosmetic can easily be removed from the skin simply with warm water (38° C. or higher, preferably 40° C. or higher) together with the makeup base.

The base film formed when the makeup base for skin of the present invention is applied to the skin has a good adhesion to a cosmetic film formed by a makeup cosmetic for skin applied thereonto. For this reason, the base film, when simply rubbed with warm water, peels off from the skin while disintegrating homogeneously and finely and retaining the cosmetic film. Thus, makeup is smoothly removed with ease causing no slimy or uncomfortable feelings. Furthermore, makeup does not re-adhere to the skin and it prevents the skin getting dirty.

BEST MODE FOR CARRYING OUT THE INVENTION

<(a) Vinyl Acetate Polymer>

The vinyl acetate polymer is a hydrophobic film-forming polymer and also is a polyvinyl acetate, which is a homopolymer of vinyl acetate.

The vinyl acetate polymer can be manufactured by a known method but a commercial product may also be used. For example, a polymer emulsion in which the vinyl acetate polymer is dispersed in water is commercially available and can be used preferably. The vinyl acetate polymer emulsion usually has a solid content of about 35 to 55% and the particle diameter of a polyvinyl acetate particle is about 0.1 to 3 μm. An example of preferable vinyl acetate polymer emulsion is Vinyblan S-40 (Nissin Chemical Industry Co., Ltd., solid content: 40%, ethanol: 2%, water: balance).

In the present invention, such vinyl acetate polymer emulsion is incorporated to the aqueous phase, and the vinyl acetate polymer is dispersed as particles in the aqueous phase which is a continuous phase.

The vinyl acetate polymer is 0.5 to 7 mass %, preferably 1 to 5.5 mass %, as solid content in the makeup base for skin of the present invention. When a vinyl acetate polymer content is too low, the makeup base may be removed with low temperature water. Alternatively, as the base film does not peel off but dissolves when rubbed with warm water, a makeup may re-adhere to the skin. Moreover, once it dissolves, slimy sensation occurs, and smooth feeling cannot be obtained. On the other hand, when the content is too high, the feeling in use becomes poor; for example, the spreadability of the makeup base becomes poor, the makeup base becomes sticky, the base film becomes rough, or the like.

<(b) Polyhydric Alcohol>

The polyhydric alcohol used in the present invention is a water soluble saturated aliphatic alcohol having two or more, preferably 2 to 6 hydroxyl groups in a molecule (an ether bond may be contained in a molecule), and the components commonly added to cosmetics, quasi drugs, and the like can be used.

Examples of the polyhydric alcohol include trihydric alcohols (for example, glycerol and trimethylolpropane), tetrahydric alcohols (for example, diglycerol, erythritol, and pentaerythritol), pentahydric alcohols (for example, xylitol and triglycerin), hexahydric alcohols (for example, sorbitol and mannitol), and polymers thereof (for example, diglycerol, triglycerol, tetraglycerol, and polyglycerol), with glycol (alcohol which has two hydroxyl groups in a molecule) being a preferable example of the polyhydric alcohol.

Examples of the glycol include ethylene glycol, diethylene glycol, triethylene glycol, tetraethylene glycol, polyethylene glycol, propylene glycol, trimethylene glycol, dipropylene glycol, polypropylene glycol, 1,3-butylene glycol, 1,2-butylene glycol, tetramethylene glycol, and 2,3-butylene glycol.

Of these, dipropylene glycol, polypropylene glycol, 1,3-butylene glycol, and polyethylene glycol (for example, a molecular weight of 500 or less) are particularly preferable.

In the makeup base for skin of the present invention, (b) the polyhydric alcohol is 0.5 to 5.5 parts by mass, preferably 0.8 to 4 parts by mass, relative to 1 part by mass of (a) the vinyl acetate polymer. When a polyhydric alcohol content is too low with respect to the vinyl acetate polymer, the base film becomes difficult to be removed with warm water. On the other hand, when a polyhydric alcohol content is too high, the base film becomes easily removable with low temperature water, and film formability are deteriorated or the makeup base may be sticky.

<(c) Hydrophilic Nonionic Surfactant>

For the hydrophilic nonionic surfactant, those commonly added to cosmetics, quasi-drugs, or the like, may be used, and hydrophilic nonionic surfactants having an HLB of 8 or higher are preferable.

Examples of the hydrophilic nonionic surfactant include sucrose fatty acid esters, glycerol or polyglycerol fatty acid esters, propylene glycol fatty acid esters, POE sorbitan fatty acid esters, POE sorbit fatty acid esters, POE glycerol fatty acid esters, POE fatty acid esters, POE alkyl ether, POE alkyl phenyl ether, POE/POP alkyl ether, POE castor oil or POE hardened castor oil derivatives, POE beeswax/lanolin derivatives, alkanolamides, POP propylene glycol fatty acid esters, POE alkylamines, POE fatty acid amides, and alkylamidoamines, and these can be blended singly or in combinations of two or more.

A preferable example of the hydrophilic nonionic surfactant used in the present invention is a sucrose fatty acid ester. The fatty acid may be a linear or branched chain, saturated or unsaturated higher fatty acid having 12 to 22 carbon atoms.

Further, other preferable examples are silicone nonionic surfactants, and examples include polyoxyethylene modified organopolysiloxanes such as KF-6011 (Shin-Etsu Chemical Co., Ltd., INCI name: PEG-11 methyl ether dimethicone).

(c) The hydrophilic nonionic surfactant is 1 to 5 mass %, preferably 1.5 to 4.5 mass %, in the makeup base of the present invention. When a hydrophilic nonionic surfactant content is too low, the makeup base is still removable with warm water of 38° C. but intense rubbing is required. In addition, the base film does not homogeneously or finely disintegrate but is removed in the form of films, flakes, or lumps, causing poor washing comfort. On the other hand, when a hydrophilic nonionic surfactant content is too high, the makeup base is becomes sticky and easily removable with low temperature water.

Additionally, the makeup base of the present invention may contain surfactants other than the hydrophilic nonionic surfactants as long as the effect of the present invention is not impaired. However, an ionic surfactant is added preferably in a modest amount, and more preferably no ionic surfactant is added, since ionic surfactants may remarkably impair the effect of the present invention.

<Other Components>

In the present invention, components routinely used for cosmetics and quasi-drugs can be blended in addition to the above essential components in the quality and quantity range within which the effect of the present invention is not impaired. Examples include oils such as liquid oils and fats, solid oils and fats, waxes, hydrocarbons, ester oils, higher fatty acids, higher alcohols, silicone oils and the like.

The makeup base for skin of the present invention is an aqueous cosmetic comprising an aqueous phase as a continuous phase, and the vinyl acetate polymer is dispersed as particles in the aqueous phase. When an oil is blended, an O/W emulsion is preferably formed in which oil-containing oil phase particles are emulsified and dispersed in the continuous aqueous phases, the oil phase particles are preferably dispersed, separately from vinyl acetate polymer particles, in the aqueous phases. When the vinyl acetate polymer is present in the dissolution state in the oil phase, the makeup base may not be removed with warm water of 38° C. Such an O/W emulsion can be obtained preferably by preparing O/W emulsion that does not contain a vinyl acetate polymer and adding a vinyl acetate polymer emulsion thereto.

Further, powder component, moisturizer, water soluble polymer, thickener, film agent, ultraviolet absorber, sequestering agent, lower alcohol, sugar, amino acid, organic amine, polymer emulsion, pH adjusting agent, skin nutrient, vitamin, antioxidant, antioxidant assistant, perfume, and/or the like, can be blended as long as the effect of the present invention is not impaired.

The makeup base for skin of the present invention is applied to the skin before applying makeup cosmetic for skin such as foundation. The makeup base of the present invention is resistant against low temperature water and, when pressed under a wet state with sweat or water, it is not removed or does not come off if the press is light. On the other hand, as the base film peels off completely from the skin while disintegrating homogeneously and finely and keeping the makeup cosmetic film by simply rubbing with fingers or palms with warm water of 38° C. or higher, preferably 40° C. or higher, makeup can be removed simply with warm water without using a cleanser such as a makeup remover or a face wash. Moreover, there is no re-adhesion of makeup to the skin. In addition, when a makeup is removed with warm water, a cloth, gauze, cotton, or the like can also be used. In the light of burdens imposed on the skin and heat stimulation, warm water should generally be 45° C. or lower.

EXAMPLES

Hereinafter, the present invention is further described with reference to specific examples, but is not limited thereto. The amount of addition is in mass % unless specified otherwise. Test methods employed in the present invention are as follows.

(Film Formability)

Using a doctor blade, a sample was pulled down to a thickness of 0.175 mm on a slide glass and dried at 37° C. all day and night. The base film formed was observed with naked eyes and evaluated by the following criteria.

◯: Dry homogeneous film without lumps (foreign substances), wrinkles, pores, and the like was formed.

Δ: Dry, almost homogeneous film with almost no lumps (foreign substances), wrinkles, pores, and the like was formed.

X: Dry inhomogeneous film with lumps (foreign substances), wrinkles, pores, and the like was formed.

XX: Dry film was not formed, but sticky film was formed.

(Resistance at 35° C.)

To investigate the resistance against sweat or the like, an immersion test in water of 35° C. was carried out. Specifically, the dry film obtained by the film formability test was immersed in water of 35° C. together with the slide glass, immediately followed by pulling it up, and such an operation was repeated for 10 times. The film immediately after a 10th operation was observed with naked eyes for any removal or coming off (immediately after immersion). Further, after allowed to stand at room temperature for 1 minute, the film was lightly rubbed with fingers and observed with naked eyes for removal or coming off (when rubbed). The observation results were evaluated by the following criteria.

◯: No removal or coming off is detected.

Δ: Almost no removal or coming off is detected.

X: Removal or coming off is detected.

(Removal at 40° C.)

To investigate the removal with warm water, the film obtained by the film formability test was immersed in warm water of 40° C. together with the slide glass and rubbed with fingers. It was observed whether there were any removal from the slide glass (removability), and, if removed, how it was removed (disintegrability), and the evaluation was made by the following criteria.

Removability

◯: Removed completely when lightly rubbed.

Δ: Not completely removed when lightly rubbed but removed completely when firmly rubbed.

X: Not removed even when firmly rubbed.

Disintegrability

In the case where it was removed in the removability evaluation, the evaluation was made by the following criteria.

◯: Base film peeled off and was removed while homogeneously and finely disintegrating.

Δ: Base film peeled off and was removed while almost homogeneously and finely disintegrating.

X: Base film did not homogeneously or finely disintegrate but peeled off and was removed in the form of films, flakes, or lumps.

XX: Base film did not peel off but was removed while dissolving with sliminess.

(Feeling in Use)

Four items of "spreadability", "unstickiness", and "foreign substance feeling (lumps)" when applied to the skin, and "lack of roughness" of the base film formed were evaluated by the following criteria.

◯: Excellent in all the items.

Δ: At least one item is rather poor.

X: At least one item is poor.

TABLE 1

| No. | Component | 1-1 | 1-2 | 1-3 | 1-4 |
|---|---|---|---|---|---|
| 1 | Water | Balance | Balance | Balance | Balance |
| 2 | Bentonite | 0.30 | 0.30 | 0.30 | 0.30 |
| 3 | POE(20) sorbitan monostearate (HLB14.9) | 1.00 | 1.00 | — | 1.00 |
| 4 | (Isobutylene/sodium maleate) copolymer | 0.05 | 0.05 | 0.05 | 0.05 |
| 5 | Dipropylene glycol | 5.00 | — | 5.00 | 5.00 |
| 6 | Sucrose stearate (HLB16) | 2.00 | 2.00 | — | 2.00 |
| 7 | Batyl alcohol | 1.00 | 1.00 | 1.00 | 1.00 |
| 8 | (Metyl methacrylate/methacrylic acid (PEG-4/PPG-3)) crosspolymer | 3.00 | 3.00 | 3.00 | 3.00 |

TABLE 1-continued

| No. | Component | 1-1 | 1-2 | 1-3 | 1-4 |
|---|---|---|---|---|---|
| 9 | Methyl polysiloxane (1 mm$^2$/s) | 10.00 | 10.00 | 10.00 | 10.00 |
| 10 | Methyl polysiloxane (2 mm$^2$/s) | 10.00 | 10.00 | 10.00 | 10.00 |
| 11 | Sucrose tetrastearate triacetate | 3.00 | 3.00 | 3.00 | 3.00 |
| 12 | Sorbitan stearate (HLB4.7) | 1.00 | 1.00 | 1.00 | 1.00 |
| 13 | Microcrystalline wax | 1.00 | 1.00 | 1.00 | 1.00 |
| 14 | Vinyl acetate polymer emulsion *1 | 7.00 | 7.00 | 7.00 | — |
| | Total | 100.00 | 100.00 | 100.00 | 100.00 |
| | Film formability | ◯ | ◯ | ◯ | ◯ |
| | Resistance at 35° C. (immediately after immersion) | ◯ | ◯ | ◯ | x |
| | Resistance at 35° C. (when rubbed) | ◯ | ◯ | ◯ | x |
| | Removal at 40° C. (removability) | ◯ | x | Δ | ◯ |
| | Removal at 40° C. (disintegrability) | ◯ | — | x | xx |

*1: VINYBLAN S-40 (Nissin Chemical Industry Co., Ltd., solid content: about 40%)

(Manufacturing Method)

3 to 7 were added to 1 and dissolved by heating, 2 was then added thereto and dispersed, and further 8 was added thereto and dispersed (aqueous phase). 11 to 13 were added to 9 and 10 and dissolved by heating (oil phase), the oil phase was fed to the heated aqueous phase and emulsified with a homomixer. 14 was mixed with the obtained O/W emulsion and obtained a makeup base.

A makeup base for skin were prepared with the compositions shown in above-described Table 1.

As shown in Sample 1-1, when a vinyl acetate polymer, polyhydric alcohol, and a hydrophilic nonionic surfactant were contained, a homogeneous base film which is not removed and does not come off with water of 35° C. was formed. Further, when rubbed in warm water of 40° C., the obtained base film was removed while homogeneously and finely disintegrating by being rubbed lightly, resulting in smooth and excellent washing comfort.

In contrast, when polyhydric alcohol was not blended as shown in Sample 1-2, the base film was not removed with water of 35° C. or warm water of 40° C.

When a hydrophilic nonionic surfactant was not blended as shown in Sample 1-3, the base film which was not removed or did not come off with water of 35° C. but was removable with warm water of 40° C. when rubbed was obtained. However, it was not removable unless it was rubbed firmly. Further, when removed, the base film did not homogeneously or finely disintegrate but was removed in the form of films, flakes, or lumps, causing uncomfortable feeling, and washing comfort was poor.

When the vinyl acetate polymer was not blended as shown in Sample 1-4, only a base film which is removable with water of 35° C. and warm water of 40° C. was obtained, and such a base film, when removed, did not peel off but dissolved with slimy sensation.

From the above, it was considered that blending a vinyl acetate polymer, polyhydric alcohol and a hydrophilic nonionic surfactant is important. Thus, each component was studied.

First, the vinyl acetate polymer was studied.

TABLE 2

| No. | Component | 2-1 | 2-2 | 2-3 | 2-4 | 2-5 | 2-6 | 2-7 |
|---|---|---|---|---|---|---|---|---|
| 1 | Water | Balance | Balance | Balance | Balance | Balance | Balance | Balance |
| 2 | Bentonite | 0.30 | 0.30 | 0.30 | 0.30 | 0.30 | 0.30 | 0.30 |
| 3 | POE (20) sorbitan monostearate (HLB14.9) | 1.00 | 1.00 | 1.00 | 1.00 | 1.00 | 1.00 | 1.00 |

TABLE 2-continued

| No. | Component | 2-1 | 2-2 | 2-3 | 2-4 | 2-5 | 2-6 | 2-7 |
|---|---|---|---|---|---|---|---|---|
| 4 | (Isobutylene/sodium maleate) copolymer | 0.05 | 0.05 | 0.05 | 0.05 | 0.05 | 0.05 | 0.05 |
| 5 | Dipropylene glycol | 5.00 | 5.00 | 5.00 | 5.00 | 5.00 | 5.00 | 5.00 |
| 6 | Sucrose stearate (HLB16) | 2.00 | 2.00 | 2.00 | 2.00 | 2.00 | 2.00 | 2.00 |
| 7 | Batyl alcohol | 1.00 | 1.00 | 1.00 | 1.00 | 1.00 | 1.00 | 1.00 |
| 8 | (Metyl methacrylate/methacrylic acid (PEG-4/PPG-3)) cross polymer | 3.00 | 3.00 | 3.00 | 3.00 | 3.00 | 3.00 | 3.00 |
| 9 | Methyl polysiloxane (1 mm$^2$/s) | 10.00 | 10.00 | 10.00 | 10.00 | 10.00 | 10.00 | 10.00 |
| 10 | Methyl polysiloxane (2 mm$^2$/s) | 10.00 | 10.00 | 10.00 | 10.00 | 10.00 | 10.00 | 10.00 |
| 11 | Sucrose tetrastearate triacetate | 3.00 | 3.00 | 3.00 | 3.00 | 3.00 | 3.00 | 3.00 |
| 12 | Sorbitan stearate (HLB4.7) | 1.00 | 1.00 | 1.00 | 1.00 | 1.00 | 1.00 | 1.00 |
| 13 | Microcrystalline wax | 1.00 | 1.00 | 1.00 | 1.00 | 1.00 | 1.00 | 1.00 |
| 14 | Vinyl acetate polymer emulsion *1 | 1.00 | 2.50 | 5.50 | 7.00 | 12.50 | 15.00 | 20.00 |
| | Total | 100.00 | 100.00 | 100.00 | 100.00 | 100.00 | 100.00 | 100.00 |
| | Solid content of vinyl acetate polymer | 0.4 | 1 | 2.2 | 2.8 | 5 | 6 | 8 |
| | Film formability | ○ | ○ | ○ | ○ | ○ | ○ | ○ |
| | Feeling in use | ○ | ○ | ○ | ○ | ○ | Δ | X |
| | Resistance at 35° C. (immediately after immersion) | ○ | ○ | ○ | ○ | ○ | ○ | ○ |
| | Resistance at 35° C. (when rubbed) | ○ | ○ | ○ | ○ | ○ | ○ | ○ |
| | Removal at 40° C. (removability) | ○ | ○ | ○ | ○ | ○ | ○ | ○ |
| | Removal at 40° C. (disintegrability) | X X | ○ | ○ | ○ | ○ | ○ | ○ |

In accordance with the manufacturing method shown in Table 1, makeup bases were prepared with the compositions shown in the above-described Table 2.

When the vinyl acetate polymer was blended in a predetermined amount or more, films, which were not removable with water of 35° C. but peeled off and removed with warm water of 40° C. while finely disintegrating, were able to be formed. On the other hand, when a vinyl acetate polymer content was too high, the spreadability was deteriorated, the makeup base became sticky, or the base film became rough.

For this reason, the vinyl acetate polymer is 0.5 to 7 mass %, preferably 1 to 5.5 mass %, in the total amount of the makeup base.

TABLE 3

| Polymer | 3-1 | 3-2 | 3-3 | 3-4 | 3-5 |
|---|---|---|---|---|---|
| Vinyl acetate polymer emulsion *1 | 7 | — | — | — | — |
| Trimethylsiloxysilicate *2 | — | 5.6 | — | — | — |
| Alkyl acrylate•tris(trimethylsiloxy)silylpropyl methacrylate copolymer-decamethylcyclopentasiloxane emulsion *3 | — | — | 6.2 | — | — |
| Polyvinylpolypyrrolidone *4 | — | — | — | 2.8 | — |
| Polyvinyl alcohol *5 | — | — | — | — | 2.8 |
| Solid content | 2.8 | 2.8 | 2.8 | 2.8 | 2.8 |
| Film formability | ○ | xx | xx | ○ | ○ |
| Resistance at 35° C. (immediately after immersion) | ○ | ○ | ○ | ○ | ○ |
| Resistance at 35° C. (when rubbed) | ○ | x | x | x | x |
| Removal at 40° C. (removability) | ○ | — | — | — | — |
| Removal at 40° C. (disintegrability) | ○ | — | — | — | — |

*2: SSD-R2 (solid content: 50%, solvent: decamethylcyclopentasiloxane, Shin-Etsu Chemical Co., Ltd.)
*3: Nissetsu NAD-45-D5 (solid content: 45%, dispersion medium: decamethylcyclopentasiloxane, NIPPON CARBIDE INDUSTRIES CO., INC)
*4: PVP K-30 (ISP Japan, Inc.)
*5: Gohsenol EG-05 (The Nippon Synthetic Chemical Industry Co., Ltd.)

The above-described Table 3 shows the results of cases where other film forming agents and polymers were used in place of the vinyl acetate polymer in Test Example 2-4. All cases resulted in poor resistance against water of 35° C. and caused removal and coming off. Further, trimethylsiloxysilicate, which is an oil soluble hydrophobic film forming agent, and other hydrophobic polymer emulsions caused poor film formability.

Next, polyhydric alcohols were studied.

TABLE 4

| No. | Component | 4-1 | 4-2 | 4-3 | 4-4 | 4-5 | 4-6 | 4-7 |
|---|---|---|---|---|---|---|---|---|
| 1 | Water | Balance | Balance | Balance | Balance | Balance | Balance | Balance |
| 2 | Bentonite | 0.30 | 0.30 | 0.30 | 0.30 | 0.30 | 0.30 | 0.30 |
| 3 | POE (20) sorbitan monostearate (HLB14.9) | 1.00 | 1.00 | 1.00 | 1.00 | 1.00 | 1.00 | 1.00 |

TABLE 4-continued

| No. | Component | 4-1 | 4-2 | 4-3 | 4-4 | 4-5 | 4-6 | 4-7 |
|---|---|---|---|---|---|---|---|---|
| 4 | (Isobutylene/sodium maleate) copolymer | 0.05 | 0.05 | 0.05 | 0.05 | 0.05 | 0.05 | 0.05 |
| 5 | Dipropylene glycol (DPG) | 1.00 | 1.50 | 2.50 | 5.00 | 10.00 | 14.00 | 16.50 |
| 6 | Sucrose stearate (HLB16) | 2.00 | 2.00 | 2.00 | 2.00 | 2.00 | 2.00 | 2.00 |
| 7 | Batyl alcohol | 1.00 | 1.00 | 1.00 | 1.00 | 1.00 | 1.00 | 1.00 |
| 8 | (Metyl methacrylate/methacrylic acid (PEG-4/PPG-3)) crosspolymer | 3.00 | 3.00 | 3.00 | 3.00 | 3.00 | 3.00 | 3.00 |
| 9 | Methyl polysiloxane (1 mm$^2$/s) | 10.00 | 10.00 | 10.00 | 10.00 | 10.00 | 10.00 | 10.00 |
| 10 | Methyl polysiloxane (2 mm$^2$/s) | 10.00 | 10.00 | 10.00 | 10.00 | 10.00 | 10.00 | 10.00 |
| 11 | Sucrose tetrastearate triacetate | 3.00 | 3.00 | 3.00 | 3.00 | 3.00 | 3.00 | 3.00 |
| 12 | Sorbitan stearate (HLB4.7) | 1.00 | 1.00 | 1.00 | 1.00 | 1.00 | 1.00 | 1.00 |
| 13 | Microcrystalline wax | 1.00 | 1.00 | 1.00 | 1.00 | 1.00 | 1.00 | 1.00 |
| 14 | Vinyl acetate polymer emulsion *1 | 7.00 | 7.00 | 7.00 | 7.00 | 7.00 | 7.00 | 7.00 |
| | Total | 100.00 | 100.00 | 100.00 | 100.00 | 100.00 | 100.00 | 100.00 |
| | Solid content of vinyl acetate polymer | 2.8 | 2.8 | 2.8 | 2.8 | 2.8 | 2.8 | 2.8 |
| | DPG/vinyl acetate polymer (mass ratio) | 0.36 | 0.54 | 0.89 | 1.79 | 3.57 | 5.00 | 5.89 |
| | Film formability | ○ | ○ | ○ | ○ | ○ | ○ | Δ |
| | Feeling in use | ○ | ○ | ○ | ○ | ○ | ○ | Δ |
| | Resistance at 35° C. (immediately after immersion) | ○ | ○ | ○ | ○ | ○ | Δ | X |
| | Resistance at 35° C. (when rubbed) | ○ | ○ | ○ | ○ | ○ | Δ | X |
| | Removal at 40° C. (removability) | X | Δ | ○ | ○ | ○ | ○ | ○ |
| | Removal at 40° C. (disintegrability) | — | Δ | ○ | ○ | ○ | ○ | ○ |

Makeup bases were prepared with the compositions shown in the above-described Table 4 in accordance with the manufacturing method shown in Table 1.

When a polyhydric alcohol content is too low with respect to the vinyl acetate polymer, the makeup base tend to become more difficult to remove with warm water of 40° C. On the other hand, when a polyhydric alcohol content is too high, water resistance at 35° C. is deteriorated, and the film formability tend to become poor or the makeup base tend to be sticky.

For this reason, it was considered that the polyhydric alcohol is 0.5 to 5.5 parts by mass, preferably 0.8 to 4 parts by mass, relative to 1 part by mass of the vinyl acetate polymer.

TABLE 5

| Polyhydric alcohol | 5-1 | 5-2 | 5-3 | 5-4 | 5-5 | 5-6 |
|---|---|---|---|---|---|---|
| Dipropelene glycol | 5.00 | — | — | — | — | — |
| Propelene glycol | — | 5.00 | — | — | — | — |
| 1,3-butylene glycol | — | — | 5.00 | — | — | — |
| Polyethylene glycol 400 | — | — | — | 5.00 | — | — |
| Glycerol | — | — | — | — | 5.00 | — |
| Diglycerol | — | — | — | — | — | 5.00 |
| Film formability | ○ | ○ | ○ | ○ | ○ | Δ (lumps) |
| Feeling in use | ○ | ○ | ○ | ○ | Δ (sticky) | Δ (foreign substance feeling) |
| Resistance at 35° C. (immediately after immersion) | ○ | ○ | ○ | ○ | ○ | ○ |
| Resistance at 35° C. (when rubbed) | ○ | ○ | ○ | ○ | Δ | Δ |
| Removal at 40° C. (removability) | ○ | ○ | ○ | ○ | ○ | ○ |
| Removal at 40° C. (disintegrability) | ○ | ○ | ○ | ○ | ○ | ○ |

The above-described Table 5 shows the results of cases where other polyhydric alcohols were used in place of dipropylene glycol in Test Example 2-4.

Propylene glycol, 1,3-butylene glycol, and polyethylene glycol 400 had almost the same results as that of dipropylene glycol. Further, glycerol and diglycerol caused slightly poorer resistance against water of 35° C. than dipropylene glycol and the like. Glycerol also resulted in a slightly sticky makeup base, and diglycerol caused insignificant foreign substances. However, these makeup bases were of a usable level.

Further, the hydrophilic nonionic surfactants were studied.

TABLE 6

| No. | Component | 6-1 | 6-2 | 6-3 | 6-4 | 6-5 | 6-6 | 6-7 |
|---|---|---|---|---|---|---|---|---|
| 1 | Water | Balance | Balance | Balance | Balance | Balance | Balance | Balance |
| 2 | Bentonite | 0.30 | 0.30 | 0.30 | 0.30 | 0.30 | 0.30 | 0.30 |
| 3 | POE (20) sorbitan monostearate (HLB14.9) | — | — | — | — | — | — | — |

TABLE 6-continued

| No. | Component | 6-1 | 6-2 | 6-3 | 6-4 | 6-5 | 6-6 | 6-7 |
|---|---|---|---|---|---|---|---|---|
| 4 | (Isobutylene/sodium copolymer | 0.05 | 0.05 | 0.05 | 0.05 | 0.05 | 0.05 | 0.05 |
| 5 | Dipropylene glycol | 1.00 | 1.50 | 2.50 | 5.00 | 10.00 | 14.00 | 16.50 |
| 6 | Sucrose stearate (HLB16) | — | — | — | — | — | — | — |
| 7 | Batyl alcohol | 1.00 | 1.00 | 1.00 | 1.00 | 1.00 | 1.00 | 1.00 |
| 8 | (Metyl methacrylate/methacrylic acid (PEG-4/PPG-3)) crosspolymer | 3.00 | 3.00 | 3.00 | 3.00 | 3.00 | 3.00 | 3.00 |
| 9 | Methyl polysiloxane (1 mm$^2$/s) | 10.00 | 10.00 | 10.00 | 10.00 | 10.00 | 10.00 | 10.00 |
| 10 | Methyl polysiloxane (2 mm$^2$/s) | 10.00 | 10.00 | 10.00 | 10.00 | 10.00 | 10.00 | 10.00 |
| 11 | Sucrose tetrastearate triacetate | 3.00 | 3.00 | 3.00 | 3.00 | 3.00 | 3.00 | 3.00 |
| 12 | Sorbitan stearate (HLB4.7) | 1.00 | 1.00 | 1.00 | 1.00 | 1.00 | 1.00 | 1.00 |
| 13 | Microcrystalline wax | 1.00 | 1.00 | 1.00 | 1.00 | 1.00 | 1.00 | 1.00 |
| 14 | Vinyl acetate polymer emulsion *1 | 7.00 | 7.00 | 7.00 | 7.00 | 7.00 | 7.00 | 7.00 |
| | Total | 100.00 | 100.00 | 100.00 | 100.00 | 100.00 | 100.00 | 100.00 |
| | Solid content of vinyl acetate polymer | 2.8 | 2.8 | 2.8 | 2.8 | 2.8 | 2.8 | 2.8 |
| | DPG/vinyl acetate polymer (mass ratio) | 0.36 | 0.54 | 0.89 | 1.79 | 3.57 | 5.00 | 5.89 |
| | Film formability | ○ | ○ | ○ | ○ | ○ | ○ | Δ |
| | Feeling in use | ○ | ○ | ○ | ○ | ○ | ○ | Δ |
| | Resistance at 35° C. (immediately after immersion) | ○ | ○ | ○ | ○ | ○ | Δ | X |
| | Resistance at 35° C. (when rubbed) | ○ | ○ | ○ | ○ | ○ | Δ | X |
| | Removal at 40° C. (removability) | X | Δ | Δ | Δ | Δ | Δ | Δ |
| | Removal at 40° C. (disintegrability) | — | X | X | X | X | Δ | X X |

The above-described Table 6 shows the results of cases where the hydrophilic nonionic surfactant was not blended in the above-described Table 4. When the hydrophilic nonionic surfactant is not blended but a polyhydric alcohol ratio to the vinyl acetate polymer is high, the base film is removable with warm water of 40° C. but not removed easily unless rubbed firmly. When the ratio of the polyhydric alcohol is significantly high, the base film is likely to be removed with water of 35° C., and the film formability, feeling in use, and the like are also deteriorated.

Therefore, it is considered to be necessary that the polyhydric alcohol is blended in a specific ratio to the vinyl acetate polymer, and a hydrophilic nonionic surfactant is also blended.

TABLE 7

| No. | Component | 7-1 | 7-2 | 7-3 | 7-4 | 7-5 | 7-6 | 7-7 |
|---|---|---|---|---|---|---|---|---|
| 1 | Water | Balance | Balance | Balance | Balance | Balance | Balance | Balance |
| 2 | Bentonite | 0.30 | 0.30 | 0.30 | 0.30 | 0.30 | 0.30 | 0.30 |
| 3 | POE (20) sorbitan monostearate (HLB14.9) | — | 1.00 | — | — | 1.00 | — | — |
| 4 | (Isobutylene/sodium maleate) copolymer | 0.05 | 0.05 | 0.05 | 0.05 | 0.05 | 0.05 | 0.05 |
| 5 | Dipropylene glycol | 5.00 | 5.00 | 5.00 | 5.00 | 5.00 | 5.00 | 5.00 |
| 6 | Sucrose stearate (HLB16) | — | — | 1.00 | 2.00 | 2.00 | 4.00 | 5.00 |
| 7 | Batyl alcohol | 1.00 | 1.00 | 1.00 | 1.00 | 1.00 | 1.00 | 1.00 |
| 8 | (Metyl methacrylate/methacrylic acid (PEG-4/PPG-3)) crosspolymer | 3.00 | 3.00 | 3.00 | 3.00 | 3.00 | 3.00 | 3.00 |
| 9 | Methyl polysiloxane (1 mm$^2$/s) | 10.00 | 10.00 | 10.00 | 10.00 | 10.00 | 10.00 | 10.00 |
| 10 | Methyl polysiloxane (2 mm$^2$/s) | 10.00 | 10.00 | 10.00 | 10.00 | 10.00 | 10.00 | 10.00 |
| 11 | Sucrose tetrastearate triacetate | 3.00 | 3.00 | 3.00 | 3.00 | 3.00 | 3.00 | 3.00 |
| 12 | Sorbitan stearate (HLB4.7) | 1.00 | 1.00 | 1.00 | 1.00 | 1.00 | 1.00 | 1.00 |
| 13 | Microcrystalline wax | 1.00 | 1.00 | 1.00 | 1.00 | 1.00 | 1.00 | 1.00 |
| 14 | Vinyl acetate polymer emulsion *1 | 7.00 | 7.00 | 7.00 | 7.00 | 7.00 | 7.00 | 7.00 |
| | Total | 100.00 | 100.00 | 100.00 | 100.00 | 100.00 | 100.00 | 100.00 |
| | Film formability | ○ | ○ | ○ | ○ | ○ | ○ | ○ |
| | Feeling in use | ○ | ○ | ○ | ○ | ○ | ○ | Δ |
| | Resistance at 35° C. (immediately after immersion) | ○ | ○ | ○ | ○ | ○ | ○ | ○ |
| | Resistance at 35° C. (when rubbed) | ○ | Δ | ○ | ○ | ○ | ○ | Δ |
| | Removal at 40° C. (removability) | Δ | ○ | ○ | ○ | ○ | ○ | ○ |
| | Removal at 40° C. (disintegrability) | X | Δ | ○ | ○ | ○ | ○ | ○ |

The above-described Table 7 shows the results of cases where the hydrophilic nonionic surfactants were blended in different amounts. The preparation was carried out in accordance with the manufacturing method as shown in Table 1.

When a hydrophilic nonionic surfactant content is too low, the makeup base is not removable with warm water of 40° C. unless rubbed firmly, and when removed, the base film does not homogeneously and finely disintegrate but is removed in the form of films, flakes, or lumps, causing poor washing comfort. On the other hand, when a hydrophilic nonionic surfactant content is too high, stickiness is caused and the resistance against water of 35° C. tends to be lower.

In conclusion, it was considered that the hydrophilic nonionic surfactant is 1 to 5 mass %, preferably 1.5 to 4.5 mass %, in the total amount of the makeup base.

TABLE 8

| Hydrophilic surfactant | 8-1 | 8-2 | 8-3 | 8-4 | 8-5 |
|---|---|---|---|---|---|
| Sucrose stearate (HLB16) | 2.00 | — | — | — | — |
| PEG-11 methyl ether dimethicone (HLB 14.5) *6 | — | 2.00 | — | — | — |
| Sodium stearoyl glutamate *7 | — | — | 2.00 | — | — |
| Lauryldimethylaminoacetic acid betaine *8 | — | — | — | 2.00 | — |
| Distearyldimethylammonium chloride *9 | — | — | — | — | 2.00 |
| Film formability | ○ | ○ | ○ | ○ | ○ |
| Feeling in use | ○ | ○ | ○ | ○ | ○ |
| Resistance at 35° C. (immediately after immersion) | ○ | ○ | x | x | ○ |
| Resistance at 35° C. (when rubbed) | ○ | ○ | x | x | ○ |
| Removal at 40° C. (removability) | ○ | ○ | ○ | ○ | x |
| Removal at 40° C. (disintegrability) | ○ | ○ | ○ | ○ | x |

*6: KF-6011 Shin-Etsu Chemical Co., Ltd.
*7: AMISOFT HS11PF, Ajinomoto Co., Inc.
*8: NISSANANON BL-ST, NOF CORPORATION
*9: CATION DS, Sanyo Chemical Industries, Ltd.

The above-described Table 8 shows the results of cases where other hydrophilic surfactants were used in place of sucrose stearate in Test Example 7-5. When an anionic surfactant or an amphoteric surfactant was blended, the resistance against water of 35° C. became lower. On the other hand, when a cationic surfactant was blended, the removal with warm water of 40° C. was difficult to achieve. Therefore, it is desirable to reduce the blending quantity of an ionic surfactant, and it is more desirable that no ionic surfactant is blended.

(Practical Use Test)

By female panelists, the makeup base of the present invention was tested for practical use. Specifically, the test was carried out as follows.

At 9:30 am, the makeup base of Test Example 1-1 was applied throughout the entire face with fingers, and 1 minute later foundation was applied thereonto. After walking outdoors for about 4 hours, durability of makeup was observed with naked eyes at about 2 pm and evaluated. Subsequently, the makeup was fixed with foundation, and the panelists further spent for 4 hours outdoors and indoors as usual. At about 6 pm, the panelists each washed their faces while wetting the face with warm water of 38° C. without using a face wash but with rubbing lightly with fingers and palms, and the makeup removal was observed with naked eyes and evaluated.

The average temperature during the test was 26 to 28° C. (the maximum temperature of about 31° C.) and the average humidity was 70 to 80% (the maximum humidity of about 91%). The test was carried out by each group of 7 panelists. Foundations used and the application method thereof were as follows.

Foundation A:
MAQUILLAGE Lighting White Powdery UV (applied by sponge) (Shiseido Company, Ltd., a powder solid foundation)

Foundation B:
MAQUILLAGE Lasting Stick Foundation UV (applied by fingers) (Shiseido Company, Ltd., an oil solid foundation)

Foundation C:
MAQUILLAGE Essence Rich White Liquid UV (applied by sponge) (Shiseido Company, Ltd., an oil-in-water emulsion foundation)

Foundation D:
Integrate Mineral Watery Foundation (applied by fingers) (Shiseido Company, Ltd., a water-in-oil emulsion foundation)

When the makeup base of the present invention was applied to the skin, it was easy to spread and foreign substances such as residues were not caused.

As for the durability of makeup, in all groups that applied any of the foundations, foundations hardly peeled off, came off, or was not smeared, though the oily shine and greasiness were observed.

As for the makeup removal, in all groups that applied any of the foundations, foundations were removable thoroughly simply by lightly rubbing with warm water of 38° C. Further, re-adhesion of foundations to the skin was not observed.

Table 9 below shows the results which evaluated the makeup removal when the test was carried out in the same manner but changing the water temperatures at washing the face.

Foundation used was Shiseido Company, Ltd., Anessa Perfect UV Liquid N (oily liquid). The evaluation criteria are as follows.

Makeup Removal
○: Foundation was removed thoroughly when rubbed only with a light force.
Δ: Foundation was removed thoroughly when rubbed with a rather intense force.
X: Foundation was not removed unless rubbed with an intense force.

TABLE 9

| Water temperature (° C.) | | | | | | | | |
|---|---|---|---|---|---|---|---|---|
| 30 | 32 | 35 | 36 | 37 | 38 | 39 | 40 | 42 |
| X | X | X | Δ | Δ | ○ | ○ | ○ | ○ |

As evident in Table 9, foundation was removable thoroughly with warm water of 38° C. or higher when rubbed lightly in all groups, and the re-adhesion of foundation was not observed. On the other hand, the removal tends to be poorer when the water temperature is lower, and foundation was not removable with water of 30° C. unless rubbed rather firmly.

When the makeup base was not applied, the foundation was not removable in all groups even when rubbed firmly with warm water of 38° C. or higher.

Figure 1:
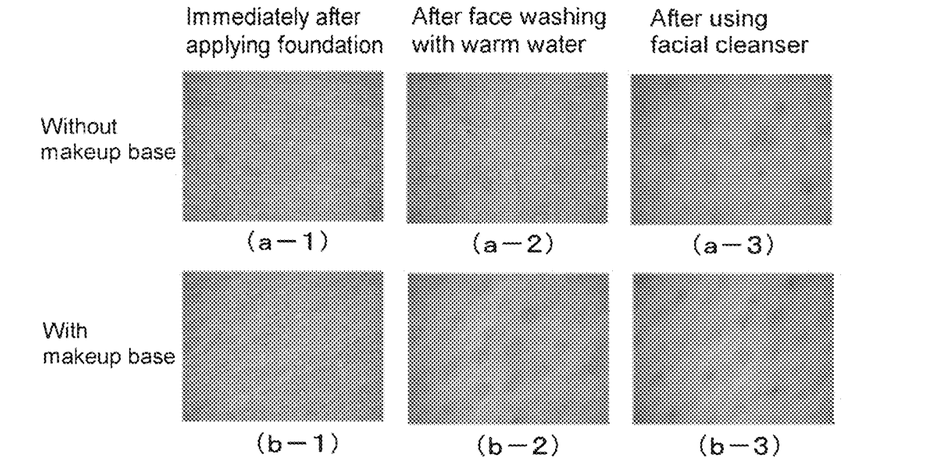
FIG. 1 are photographs showing skin conditions immediately after applying foundation, immediately after washing the face with warm water, and immediately after washing the face using a face wash, in each case of where the makeup base for skin of an example of the present invention is applied and not applied to the skin before applying foundation.

FIG. 1 is shown as the representative example. In FIG. 1, (a-1) to (b-3) are as follows.
(a-1): The skin immediately after applying Foundation A without applying the makeup base of Test Example 1-1.

(a-2): The skin immediately after washing the skin of (a-1) only with warm water of 38° C.
(a-3): The skin immediately after further washing the skin of (a-2) using a face wash.
(b-1): The skin immediately after applying Foundation A after the makeup base of Test Example 1-1.
(b-2): The skin immediately after washing the skin of (b-1) only with warm water of 38° C.
(b-3): The skin immediately after further washing the skin of (b-2) using a face wash.

As evident from FIG. 1 (a-1) to (a-3), when the makeup base of the present invention was not used, foundation was hardly removed by washing the face with warm water and was not removable unless a face wash was used.

In contrast, as evident from FIG. 1 (b-1) to (b-3), when the makeup base of the present invention was used, foundation was thoroughly removed simply by washing the face with warm water.

Additionally, when the makeup base according to the present invention is used in practice, as the base film thickness on the skin is extremely thin, it tends to become cleansable in slightly lower temperature, compared to the case where a film is formed using the doctor blade. Further, the water resistance of a makeup cosmetic applied onto the makeup base of the present invention affects the base film cleansing temperature. Therefore, when a makeup cosmetic having high water resistance is used, it is preferable that a cleansing temperature is set slightly higher.

Formula Example 1 O/W Emulsion Makeup Base

| | |
|---|---|
| Water | Balance |
| Bentonite | 0.3 mass % |
| POE (20) sorbitan monostearate | 1.0 |
| (Isobutylene/sodium maleate) copolymer | 0.05 |
| Dipropylene glycol | 5.0 |
| Sucrose stearate | 2.0 |
| Batyl alcohol | 1.0 |
| Silica filmed microparticulate titanium oxide | 5.0 |
| (Methyl methacrylate/methacrylic acid (PEG-4/PPG-3)) crosspolymer | 3.0 |
| Dimethylpolysiloxane (1 mm$^2$/s) | 10.0 |
| Dimethylpolysiloxane (2 mm$^2$/s) | 10.0 |
| Sucrose tetrastearate triacetate | 3.0 |
| Sorbitan stearate | 1.0 |
| Microcrystalline wax | 1.0 |

-continued

| | |
|---|---|
| Water | Balance |
| Octyl methoxy cinnamate | 3.0 |
| Vinyl acetate polymer emulsion *1 | 7.0 |

When applied to the skin, the makeup base for skin of Formula Example 1 was easy to spread on the skin and formed an unsticky homogeneous base film, which did not cause any foreign substances such as residues. Further, when the makeup base was applied to the skin before applying foundation, foundation was thoroughly removed by simply rubbing with warm water of 38° C. or higher without using a face wash. Furthermore, the re-adhesion of foundation to the skin was not observed.

What is claimed is:

1. A makeup method comprising:
   a step of applying a makeup base to skin,
   a step of applying a makeup cosmetic over the makeup base, and
   a step of removing the makeup cosmetic together with the makeup base, by rubbing the skin with warm water of 38 to 45° C. to remove the makeup cosmetic and the makeup base;
   wherein the makeup base comprises a water-containing aqueous phase as a continuous phase, the water-containing aqueous phase containing
   (a) vinyl acetate polymer,
   (b) polyhydric alcohol, and
   (c) hydrophilic nonionic surfactant,
   wherein the (a) vinyl acetate polymer is 0.5 to 7 mass % in the makeup base and is dispersed as particles in the water-containing aqueous phase,
   wherein the (b) polyhydric alcohol is 0.5 to 5.5 parts by mass relative to 1 part by mass of the (a) vinyl acetate polymer, and
   wherein the (c) hydrophilic nonionic surfactant is 1 to 5 mass % in the makeup base.

2. The makeup method according to claim 1, wherein the warm water does not contain cleansers.

3. The makeup method according to claim 1, wherein the (b) polyhydric alcohol is one or more selected from the group consisting of dipropylene glycol, propylene glycol, 1,3-butylene glycol, and polyethylene glycol.

* * * * *